(12) United States Patent
Fliss

(10) Patent No.: US 7,193,700 B2
(45) Date of Patent: Mar. 20, 2007

(54) APPARATUS FOR MONITORING THE FUNCTIONALITY OF AN OPTICAL ELEMENT

(75) Inventor: Stefan Fliss, Stuttgart (DE)

(73) Assignee: Trumpf Lasertechnik GmbH, Ditzingen (DE)

( * ) Notice: Subject to any disclaimer, the term of this patent is extended or adjusted under 35 U.S.C. 154(b) by 266 days.

(21) Appl. No.: 10/660,790

(22) Filed: Sep. 12, 2003

(65) Prior Publication Data

US 2004/0114134 A1 Jun. 17, 2004

(30) Foreign Application Priority Data

Sep. 12, 2002 (EP) .................................. 02020369

(51) Int. Cl.
*G01N 21/88* (2006.01)

(52) U.S. Cl. .................................. 356/239.2; 356/445
(58) Field of Classification Search ........ 356/445–448, 356/237.1, 237.2, 239.2, 239.7, 239.8, 237.3

See application file for complete search history.

(56) References Cited

U.S. PATENT DOCUMENTS

| | | | | | |
|---|---|---|---|---|---|
| 4,423,726 | A | * | 1/1984 | Imagawa et al. | ............... 606/2 |
| 4,691,106 | A | * | 9/1987 | Hyun et al. | .................. 250/349 |
| 5,159,402 | A | * | 10/1992 | Ortiz, Jr. | .................. 356/237.1 |
| 5,929,981 | A | * | 7/1999 | Keilbach | ...................... 356/73 |
| 6,496,257 | B1 | * | 12/2002 | Taniguchi et al. | ........ 356/239.2 |
| 6,549,271 | B2 | * | 4/2003 | Yasuda et al. | ................. 355/55 |

OTHER PUBLICATIONS

Dowden, S. et al., "Reflectometer for fast measurements of mirror reflectivity," Measurement Science and Technology, IOP Publishing, Bristol, GB, Bd. 8, Nr. 11, pp. 1258-1261 (1997).

Takahashi H. et al., "Automatic reflectivity map measurement of high power $CO_2$ laser optics," Optics and Laser Technology, Elsevier Science Publishers BV., Amsterdam, NL, Bd. 21, Nr. 1, pp. 37-39 (1989).

* cited by examiner

*Primary Examiner*—Richard A. Rosenberger
(74) *Attorney, Agent, or Firm*—Fish & Richardson P.C.

(57) ABSTRACT

An apparatus for monitoring the functionality of an optical element includes a detector and a light source whose radiation is reflected to the detector by a surface of the optical element facing the detector and the light source.

43 Claims, 1 Drawing Sheet

APPARATUS FOR MONITORING THE FUNCTIONALITY OF AN OPTICAL ELEMENT

CLAIM OF PRIORITY

This application claims priority under 35 USC §119(a) to patent application Ser. No. EP 02020369.1, filed on Sep. 12, 2002, the entire contents of which is hereby incorporated by reference.

TECHNICAL FIELD

The invention relates to an apparatus for monitoring the functionality of an optical element and more particularly to a laser including such a monitoring apparatus.

BACKGROUND

A laser beam that impinges on an optical element (e.g., an output coupler mirror of a laser resonator) is not entirely reflected or transmitted. Rather, a small portion of the laser beam is also absorbed by the optical element. Soiling of the optical element results in an increased absorption of the laser beam and therefore in heating of the optical element. With the high laser powers currently used, this can result in vaoprization of the respective optical element. The vapors produced by such vaporization are hazardous to health and pollute the surroundings (e.g., the laser resonator). In addition, a crack or break in an output coupler mirror with resulting vacuum leakage of a laser resonator can result in complete destruction of the laser.

German patent document DE 198 39 930 C1 discloses the use of an additional light source to monitor a protective glass. The radiation of the light source is coupled on one side of the protective glass, and the intensity of the radiation decoupled on the other, opposite side of the protection glass, where it is measured with a detector. Internal material defects of the protective glass such as cracks, can be detected by intensity changes. This monitoring apparatus is suited only for transparent optical elements. Moreover, the surface of the optical element cannot be monitored for functionality apart from the remaining optical element.

It is therefore desirable to improve the detection of functionality changes of optical elements.

SUMMARY

In a first general aspect, the invention provides an apparatus for monitoring the functionality of an optical element that includes a detector and a light source whose radiation is reflected to the detector by a surface of the optical element facing the detector and the light source.

In a second general aspect, the invention features an apparatus for monitoring the functionality of an output coupler mirror of a laser resonator. The apparatus includes a light source whose radiation is reflected by a surface of the optical coupler mirror and a detector for detecting radiation emitted from the light source and reflected by the surface of the output coupler. The detector is adapted for detecting a characteristic of the reflected radiation indicative of the functionality of the output coupler mirror.

In another aspect, a laser includes an optical element, a detector, and a light source whose radiation is reflected by a surface of the optical element facing the detector and the light source to the detector. The light source and the detector are arranged to monitor the functionality of the optical element.

Implementations can include one or more of the following features. The light source can be arranged to direct radiation to the center of the surface of the optical element. The light source and the detector can be disposed laterally to the optical element. The light source and the detector both can be disposed at the same angle to the surface of the optical element. The radiation of the light source can be directed to the surface of the optical element at an angle of less than 30°. The light source and the detector can be integrated in a holder for the optical element. The light source can be a light emitting diode and the detector can be a photodiode. The apparatus can further include a comparator for comparing a detected light intensity detected by the detector with a reference intensity. The comparator can generate an error signal when the detected light intensity differs from the reference intensity by a defined value. The optical element can include zinc selenide, gallium arsenide, or diamond. The laser can be a $CO_2$ laser. The laser can further include a laser resonator, and the surface can be an inner side or an outer surface of an output coupler mirror facing the laser resonator. The comparator can generate an error signal when the detected light intensity differs from the reference intensity by a defined value. The error signal can cause the laser to be switched off.

In a further general aspect, a method for monitoring damage to an optical element of a laser resonator includes shining a light beam onto a surface of the optical element, detecting an intensity of a reflected portion of the light beam that is reflected by the optical element, and comparing the intensity of the reflected portion of the light beam with a reference intensity.

Implementations can include one or more of the following features. The light beam can be directed to the surface of the optical element at an angle of greater than 60° to the normal of the surface of the optical element. The method can include generating an error signal when the intensity of the reflected portion of the light beam differs from the reference intensity by a defined value. The method can include switching off a laser in response to the error signal.

Further advantages of the invention are apparent from the description and the drawings. The features mentioned herein can be used either individually or collectively in arbitrary combination. The embodiments shown and described are not to be understood as an exhaustive enumeration, but rather have exemplary character for describing the invention.

DESCRIPTION OF THE DRAWINGS

Like reference symbols in the various drawings indicate like elements.

DETAILED DESCRIPTION

Figure 1:
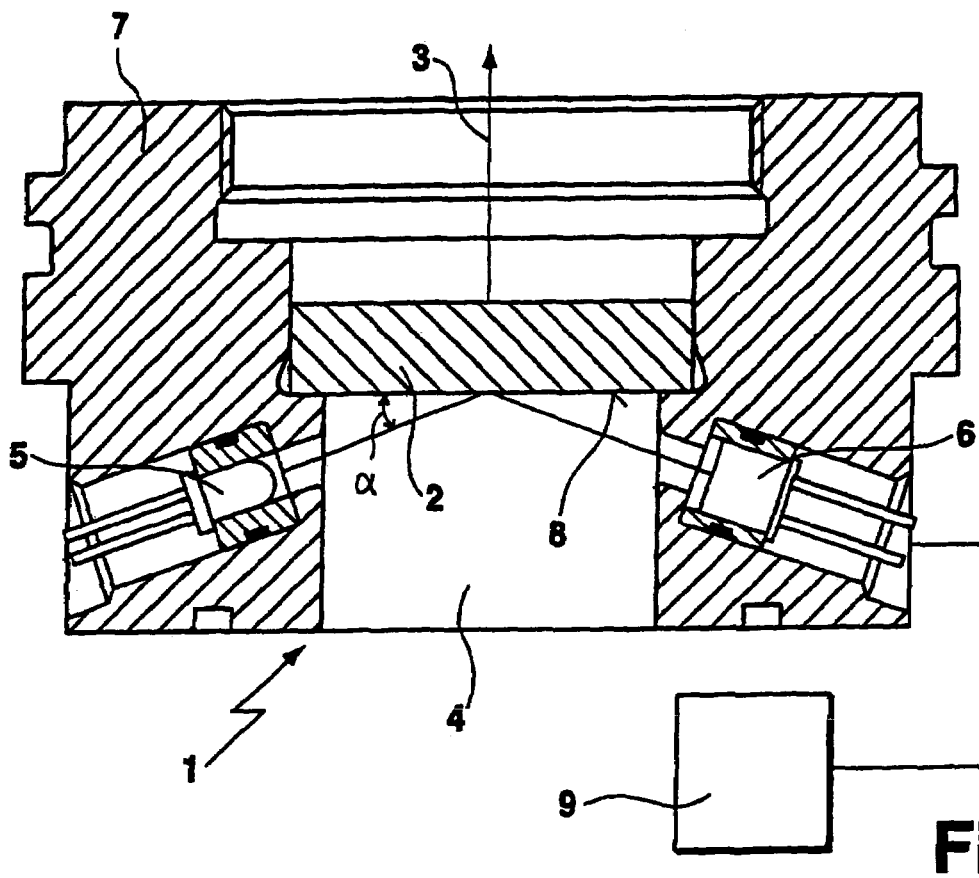
FIG. 1 is a first cross-sectional diagram of a apparatus for monitoring the output coupler mirror of a laser resonator.

The apparatus 1 shown in FIG. 1 can be used to monitor the functionality of the output coupler mirror 2 of a laser. A laser beam 3 is transmitted through the partially-transmitting output coupler mirror 2 from a laser resonator 4 in the direction to a workpiece (not shown) to be processed.

The monitoring apparatus 1 includes a light source 5 (e.g., a light emitting diode) and a detector 6 (e.g., a photodiode), which are both integrated into a holder 7 of the output coupler mirror 2 on the side of the output coupler mirror 2 facing the laser resonator 4. The light source 5 and the detector 6 are diametrically opposed relative to the output coupler mirror 2 and are disposed at the same angle to the mirror surface 8 of the output coupler mirror 2 facing the laser resonator 4 and lateral to the output coupler mirror 2. The light emitting diode 5 and the photodiode 6 simultaneously form an end of the vacuum inside of the resonator from atmosphere.

The radiation emitted by the light source 5 with a reference intensity is directed centrally onto the mirror surface 8 and at an angle, such that it is reflected by the mirror surface 8 onto the opposite detector 6. The angle can be less than 30°. The measured intensity of the reflected radiation depends on the quality of the mirror surface 8 and therefore can be used to measure the damage and aging of the mirror surface 8. The optical element 2 can be monitored during operation of a laser, when laser radiation is switched on, or during a processing break, when the laser radiation is switched off. The measured light intensity is supplied to a comparator 9 (e.g., a microprocessor) to compare the measured light intensity with a stored reference intensity. For example, the reference intensity 15 can be the light intensity measured when the output coupler mirror 2 is new. If the light intensity measured by the detector 6 differs by a defined value from the stored reference intensity, the comparator 9 outputs an error message and switches off the laser.

The wavelength of the light source generally differs from the laser wavelength (e.g., 10.6 μm for a $CO_2$ lasers). It is selected such that the surface to be monitored of the optical element reflects at least part of the radiation of the light source. It is therefore possible to monitor also optical elements which are transparent for laser wavelength for surface functionality. The optical element can be formed of zinc selenide (ZnSe), gallium arsenide (GaAs), or diamond.

For certain embodiments of the invention, the light source and the detector are disposed laterally to the optical element and at the same angle to the monitored surface of the optical element, for example, at an angle of less than 30°.

Figure 2:
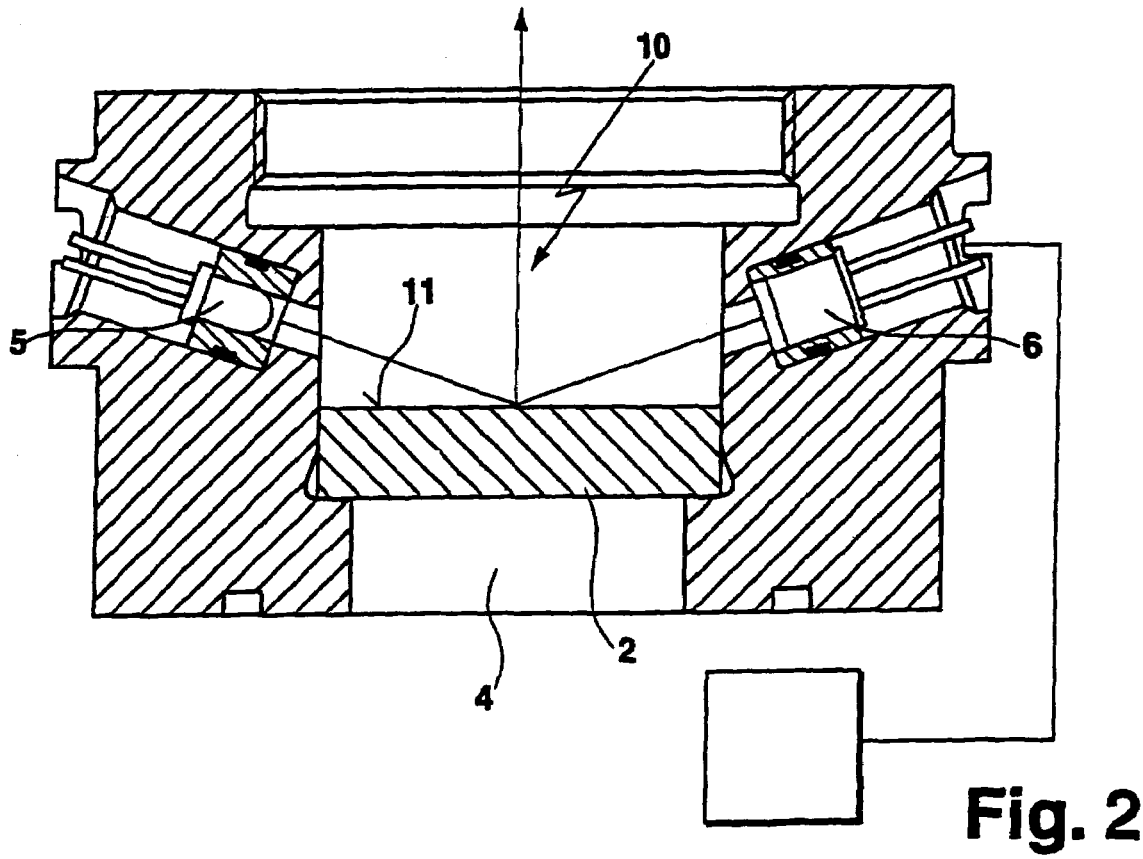
FIG. 2 is a second cross-sectional diagram of the apparatus for monitoring the output coupler mirror of a laser resonator.

The monitoring apparatus 10 of FIG. 2 differs from the monitoring apparatus 1 only in that it is disposed on the side of the output coupler mirror 2 facing away from the laser resonator 4 and therefore monitors the functionality of the other surface 11 of the output coupler mirror 2.

OTHER EMBODIMENTS

A number of embodiments of the invention have been described. Nevertheless, it will be understood that various modifications may be made. Accordingly, other embodiments are within the scope of the following claims.

What is claimed is:

1. An apparatus for monitoring the functionality of an optical element in a system comprising a laser resonator, the apparatus comprising:
    a detector; and
    a light source, configured to generate a light beam having a wavelength different from that of light emitted by the laser resonator, the light beam being at least partially reflected to the detector by a surface of the optical element facing the detector and the light source;
    wherein the light source and the detector are integrated in a holder for the optical element.

2. The apparatus of claim 1, wherein the light source is arranged to direct radiation to the center of the surface of the optical element.

3. The apparatus of claim 1, wherein the light source and the detector are disposed laterally to the optical element.

4. The apparatus of claim 1, wherein the light source and the detector are both disposed at the same angle to the surface of the optical element.

5. The apparatus of claim 1, wherein the radiation of the light source is directed to the surface of the optical element at an angle of less than 30°.

6. The apparatus of claim 1, wherein the light source is a light emitting diode and the detector is a photodiode.

7. The apparatus of claim 1, further comprising a device configured to analyze data obtained by the detector and determine whether damage to the mirror surface has occurred wherein the device comprises a comparator for comparing a detected light intensity detected by the detector with a reference intensity.

8. The apparatus of claim 7, wherein the comparator generates an error signal when the detected light intensity differs from the reference intensity by a defined value.

9. The apparatus of claim 1, wherein the optical element comprises zinc selenide.

10. The apparatus of claim 1, wherein the optical element comprises gallium arsenide.

11. The apparatus of claim 1, wherein the optical element comprises diamond.

12. The apparatus of claim 1, wherein the detector, the light source, and the optical element are exposed to a common vacuum pressure.

13. The apparatus of claim 1, wherein the light source is positioned so as to provide an unobstructed pathway to the surface of the optical element.

14. The apparatus of claim 1, wherein the detector and the light source are diametrically opposed relative to the optical element.

15. The apparatus of claim 1 wherein the optical element comprises an output coupler mirror.

16. An apparatus for monitoring the functionality of an optical element in a system comprising a laser resonator, the apparatus comprising:
    a detector; and
    a light source, configured to generate a light beam having a wavelength different from that of light emitted by the laser resonator, the light beam being at least partially reflected by a surface of the optical element to the detector, wherein the surface faces the detector and the light source, the light beam being directed to the center of the surface of the optical element,
    wherein the light source and the detector are disposed laterally to the optical element and integrated in a holder for the optical element such that, the light source and the detector are disposed at the same angle to the surface of the optical element, and the light beam is directed to the surface of the optical element at an angle of less than 30°; and
    a comparator for comparing a light intensity detected by the detector with a reference intensity and for generating an error signal when the detected light intensity differs from the reference intensity by a defined value.

17. A laser comprising:
    a laser resonator;
    an optical element toward which a laser beam is directed from the laser resonator;
    a detector; and
    a light source other than the laser resonator, configured to emit a light beam, having a wavelength different from that of the laser beam, that is at least partially reflected by a surface of the optical element facing the detector and the light source to the detector, wherein the light source and the detector are arranged to monitor the functionality of the optical element, wherein the light source and the detector are integrated in a holder for the optical element.

18. The laser of claim 17, comprising a $CO_2$ laser.

19. The laser of claim 17, wherein the surface of the optical element is a mirror surface.

20. The laser of claim 19, wherein the surface of the optical element is an inner side of an output coupler mirror facing the laser resonator.

21. The laser of claim 19, wherein the surface of the optical element is an outer side of an output coupler mirror facing away from the laser resonator.

22. The laser of claim 17, further comprising a comparator for comparing a light intensity detected by the detector with a reference intensity and generating an error signal when the detected light intensity differs from the reference intensity by a defined value.

23. The laser of claim 22, wherein the error signal causes the laser to be switched off.

24. The laser of claim 17, wherein the radiation of the light source is directed to the center of the surface of the optical element.

25. The laser of claim 17, wherein the light source and the detector are disposed laterally to the optical element.

26. The laser of claim 17, wherein the light source and the detector are disposed at the same angle to the surface of the optical element.

27. The laser of claim 17, wherein the radiation of the light source is directed to the surface of the optical element at an angle of less than 30°.

28. The apparatus of claim 17, wherein the detector, the light source, and the optical element are exposed to a common vacuum pressure.

29. The apparatus of claim 17, wherein the light source is positioned so as to provide an unobstructed pathway to the surface of the optical element.

30. The apparatus of claim 17, wherein the detector and the light source are diametrically opposed relative to the optical element.

31. An apparatus for monitoring damage to an optical element of a laser resonator, the apparatus comprising:

a light source other than the laser resonator, configured to emit a light beam, having a wavelength different from that of the laser beam, that is at least partially reflected by a surface of the optical element;

a detector for detecting radiation emitted from the light source and reflected by the surface of the optical element, wherein the detector is adapted for detecting a characteristic of the reflected radiation indicative of damage to the optical element, wherein the light source and the detector are integrated in a holder for the optical element.

32. The apparatus of claim 31, wherein the radiation of the light source is directed to the surface of the optical element at an angle of greater than 60° to the normal of the surface of the optical element.

33. The apparatus of claim 31, wherein the light source is a light emitting diode and the detector is a photodiode.

34. The apparatus of claim 31, wherein the characteristic of the reflected radiation is a light intensity of the reflected radiation, and further comprising a comparator for comparing the light intensity of the reflected radiation with a reference intensity.

35. The apparatus of claim 34, wherein the comparator generates an error signal when the light intensity of the reflected radiation differs from the reference intensity by a defined value.

36. The apparatus of claim 35, wherein the error signal is used to switch off a laser whose optical element is monitored by the apparatus.

37. The apparatus of claim 31, wherein the detector, the light source, and the optical element are exposed to a common vacuum pressure.

38. The apparatus of claim 31, wherein the light source is positioned so as to provide an unobstructed pathway to the surface of the optical element.

39. The apparatus of claim 31, wherein the detector and the light source are diametrically opposed relative to the optical element.

40. A method for monitoring damage to an optical element of a laser resonator, the method comprising:

directing a laser beam from a laser resonator towards the optical element;

shining a light beam other than the laser beam from a light source onto a surface of the optical element while the laser beam is directed towards the optical element;

detecting a light intensity of a reflected portion of the light beam that is reflected by the optical element, while shining the light beam on the surface of the optical element, using a detector that, with the light source, is integrated in a holder for the optical element; and comparing the light intensity of the reflected portion of the light beam with a reference intensity to determine whether the surface of the optical element is damaged.

41. The method of claim 35, wherein the light beam is directed to the surface of the optical element at an angle of greater than 60° to the normal of the surface of the optical element.

42. The method of claim 40, further comprising generating an error signal when the light intensity of the reflected portion of the light beam differs from the reference intensity by a defined value.

43. The method of claim 42, further comprising switching off a laser in response to the error signal.

* * * * *